US Patent [19]  
Olbrich et al.

[11] Patent Number: 4,614,808  
[45] Date of Patent: Sep. 30, 1986

[54] PROCESS FOR REACTING MALEIC ANHYDRIDE WITH VINYLBENZENES

[75] Inventors: Jürgen Olbrich, Dorsten; Jörg Dörffel, Marl, both of Fed. Rep. of Germany

[73] Assignee: Huels Aktiengesellschaft, Marl, Fed. Rep. of Germany

[21] Appl. No.: 780,876

[22] Filed: Sep. 27, 1985

[30] Foreign Application Priority Data

Sep. 27, 1984 [DE] Fed. Rep. of Germany ....... 3435429

[51] Int. Cl.$^4$ .......................................... C07D 407/04
[52] U.S. Cl. .................................... 549/236; 549/234
[58] Field of Search ............................. 549/236, 234

[56] References Cited

U.S. PATENT DOCUMENTS 3,472,875 10/1969 DiLeone .............................. 549/236
3,769,304 10/1973 Saluti et al. ........................ 549/234

FOREIGN PATENT DOCUMENTS 188581 11/1982 Japan .
170776 10/1983 Japan .

OTHER PUBLICATIONS

Miller et al., J. Am. Chem. Soc. 78:1017 (1956).
Mayo, J. Am. Chem. Soc. 80:2465 (1958).

*Primary Examiner*—Richard L. Raymond
*Attorney, Agent, or Firm*—Millen & White

[57] ABSTRACT

The reaction of maleic anhydride with vinylbenzene to form tetralin dianhydride is improved by conducting, per mole of vinyl group, 2–20 l/h of air (measured under normal conditions: 20° C./1 bar) through the reaction mixture.

17 Claims, No Drawings

PROCESS FOR REACTING MALEIC ANHYDRIDE WITH VINYLBENZENES

BACKGROUND OF THE INVENTION

This invention relates to a process for reacting maleic anhydride with optionally nuclear-substituted vinylbenzenes to form tetralin dianhydrides at an elevated temperature in the presence of a solvent and hydroquinone while pasing an oxygen-containing nitrogen stream through the reaction mixture. Tetralin dianhydrides are used for the preparation of polyimides, plasticizers for pvc or crosslinking agents for lacquers.

The reaction of maleic anhydride with vinylbenzenes to such dianhydrides has been known for a long time. In order to avoid polymerization, the process is carried out while passing an oxidizing gas through the reaction mixture. Nitrogen having a maximum oxygen proportion of 5% (U.S. Pat. No. 3,769,304) has, inter alia, been disclosed for this purpose. Although there is no explicit statement why the oxygen proportion must not be higher, a possible explanation exists in the remark that the gasous stream must not be flammable.

On the other hand, it has been known from J. Am. Chem. Soc. 78:1017 (1956) and/or 80:2465 (1958) that, with higher oxygen contents in the gaseous atmosphere, styrene is oxidized to styrene oxide or peroxide.

SUMMARY OF THE INVENTION

It is an object of this invention to simplify and improve the prior-art methods without rerouting the course of the reaction in the direction toward oxidized styrene, inter alia, and yet avoiding or decreasing polymerizations.

Upon further study of the specification and appended claims, further objects and advantages of this invention will become apparent to those skilled in the art.

These objects have been achieved in the finding that unexpectedly the reaction is still possible even if, per mole of vinyl group (including any additional vinyl groups on styrene but not considering the double band in maleic anhydride), 2–20 l/h of air (measured under normal conditions: 20° C./1 bar) is conducted through the reaction mixture. In a preferred version, 3–10 l/h of air is passed through.

Thus, this invention relates to a process for the reaction of maleic anhydride with optionally nuclear-substituted vinylbenzenes to form tetralin dianhydrides at an elevated temperature in the presence of a solvent and a hydroquinone while passing an oxygen-containing nitrogen stream through the reaction mixture, wherein per mole of vinyl group, 2–20 l/h of air (measured under normal conditions: 20° C./1 bar) is conducted through the reaction mixture.

DETAILED DISCUSSION OF THE INVENTION

In addition to the maleic anhydride, optionally nuclear-substituted vinylbenzenes and divinylbenzenes are employed; in the latter, the vinyl groups can be arranged in the o-, m- or p-position. Suitable substituents on these vinylbenzenes primarily include alkyl residues of 1–7 carbon atoms also in the o-, m-, or p-position. In addition to individual vinylbenzenes, mixtures of such vinylbenzenes can also be utilized. Although the divinylbenzene can be substituted as indicated above, it is preferred that unsubstituted divinylbenzene be utilized.

Maleic anhydride and the vinylbenzene can be used in a molar ratio of 2:0.7 to 2:1.3, preferably 2:0.95 to 2:1.1. Increasing the maleic anhydride proportion in the mixture past the indicated ratio range leads to formation of undesirable cycloaliphatic compounds. Lowering this proportion leads to the formation of polyvinylbenzenes.

Hydroquinone is added to the mixture as a further inhibitor against polymerization. In place of hydroquinone, it is, of course, also possible to utilize its derivatives, for example, tolyl hydroquinone, ethyl hydroquinone, isopropyl hydroquinone, di-tert-butyl hydroquinone, or similar compounds. The concentration of these additives is 0.4–1% by weight, based on the total weight of maleic anhydride and vinylbenzene.

The reaction temperatures are in the range of about 90° and 140° C., preferably 105° to 125° C. and times are in the range of 5 to 6 hours.

The reaction is conducted in solution. Suitable solvents include all those which are inert, e.g., having a boiling point higher than the reaction temperature. The boiling point is in a range From about 100° to 180° C. Suitable examples include hydrocarbon (cyclo)aliphatic solvents, e.g., octane, decane, dimethylhexane, dimethylcyclohexane, methylcyclohexane, hydrocarbon aromatic solvents, for example, toluene, xylene, benzene, etc.

The concentration of maleic anhydride in the solvent is 40–90% by weight, preferably 48–60% by weight.

Of course, it is not necessary that air be utilized in this invention; rather, any reaction compatible gas mixture containing 6–21 weight percent of oxygen can be utilized under the conditions of this invention.

The manufacturing process is described below in general terms; the process is not intended to be limited to this operating method. Therein, a solution is prepared from maleic anhydride and hydroquinone. While air is introduced, the mixture is brought to the selected reaction temperature. Then vinylbenzene is added in such a way that the reaction temperature does not rise to a substantial extent. After termination of the reaction and cooling of the reaction mixture, the precipitated final product is filtered off and subsequently recrystallized. Acetonitrile or a toluene/acetone mixture, for example, is very highly suitable for recrystalliztion.

The yield of final product (dianhydride) per this invention is high, e.g., up to 90% by weight or more.

All details of the process of this invention, unless indicated otherwise herein, are conventional, e.g., as described in U.S. Pat. No. 3,769,304 or in U.S. Pat. No. 3,472,875 which disclosure is incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

294 g of maleic anhydride, 340 ml of toluene and 2.4 g of hydroquinone are heated to a temperature of 120° C. while 15 l/h of air is introduced (measured under normal conditions: 20° C./1 bar), and then the mixture is gradually combined with 156 g of styrene. Addition of styrene takes place in such a way that the temperature of the reaction mixture remains constant. After addition of styrene is finished, the reaction mixture is maintained for 5 hours at 120° C. and filtered after cooling.

The filter residue, after recrystallization from a toluene/acetone mixture (volume proportion 5:1), yields 351 g (78% by weight) of white 3,4-dicarboxy-1,2,3,4-tetrahydro-1-naphthalenesuccinic acid dianhydride ("Tetralin Dianhydride") having a melting point of 202°–204° C.

EXAMPLE 2

Conducting the reaction analogously to Example 1 while passing 5 l/h of air through the reaction mixture yields 333 g (74% by weight) of "Tetralin Dianhydride".

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process comprising reacting maleic anhydride with vinylbenzene, divinylbenzene, or a nuclear substituted derivative thereof to form the corresponding tetralin dianhydride, at an elevated temperature, in a reaction-compatible solvent, and in the presence of an inhibitor-effective amount of a hydroquinone,
   the improvement comprising passing through the reaction mixture, per mole of vinyl group in the vinylbenzene reactant, 2–20 l/h of air (measured under normal conditions: 20° C./1 bar).

2. A process of claim 1, wherein 3–10 l/h of air (measured under normal conditions) is passed through the reaction mixture.

3. A process of claim 1 comprising reacting maleic anhydride and vinylbenzene.

4. A process of claim 1, wherein divinylbenzene is a reactant.

5. A process of claim 1, wherein vinylbenzene or divinylbenzene substituted by $C_{1-7}$-alkyl is a reactant.

6. A process of claim 1, wherein the molecular ratio of maleic anhydride to the vinylbenzene is from about 2:0.7 to about 2:1.3.

7. A process of claim 6, wherein said ratio is from about 2:0.95 to about 2:1.1.

8. A process of claim 7, wherein the reactants are maleic anhydride and vinylbenzene.

9. A process of claim 1, wherein the hydroquinone is hydroquinone or alkylhydroquinone.

10. A process of claim 1, wherein the amount of hydroquinone is 0.4–1% by weight based on the total weight of maleic anhydride and the vinylbenzene.

11. A process of claim 1, wherein the reaction temperature is 90°–140° C.

12. A process of claim 1, wherein the reaction temperature is 105°–125° C.

13. A process of claim 1, wherein the solvent is hydrocarbon aliphatic or hydrocarbon aromatic.

14. A process of claim 1, wherein the solvent is octane, decane, dimethylhexane, dimethylcyclohexane, methylcyclohexane, toluene, xylene or benzene.

15. A process of claim 1, wherein the concentration of maleic anhydride in the solvent is 40–90% by weight.

16. In a process comprising reacting maleic anhydride with vinylbenzene, divinylbenzene or a nuclear substituted derivative thereof to form the corresponding tetralin dianhydride, at an elevated temperature, in a reaction-compatible solvent, and in the presence of an inhibitor-effective amount of tolyl hydroquinone, ethyl hydroquinone, isopropyl hydroquinone, or di-tert-butyl hydroquinone,
   the improvement comprising passing through the reaction mixture, per mole of vinyl group in the vinylbenzene reactant, 2–20 l/h of air (measured under normal conditions: 20° C./1 bar).

17. A process comprising reacting maleic anhydride and vinylbenzene in a molar ratio, respectively, of 2:0.7 to 2:1.3, at a temperature of 90°–140° C., in a reaction-compatible solvent, in the presence of an inhibitor-effective amount of hydroquinone, while passing through the reaction mixture 2–20 l/h of air (measured under normal conditions: 20° C./1bar) per mole of vinyl groups in the vinylbenzene reactant.

* * * * *